Figure 1:
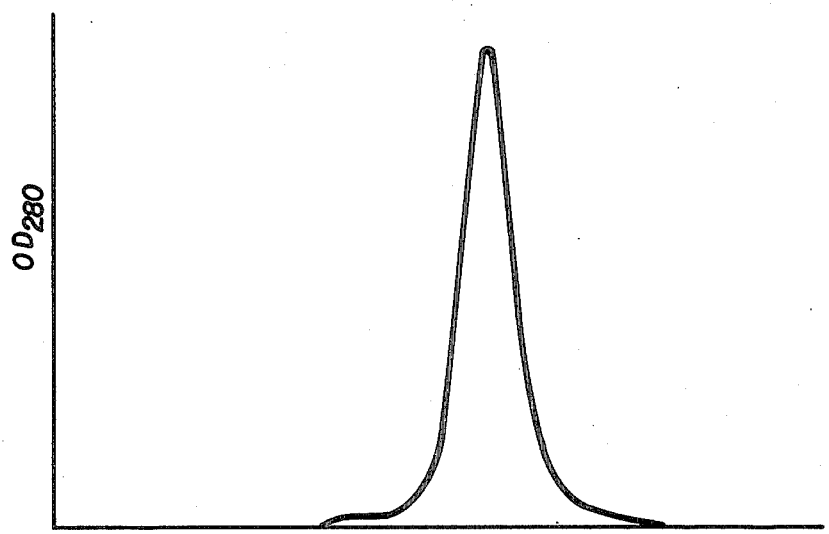

United States Patent [19]

Sato et al.

[11] 4,384,993

[45] May 24, 1983

[54] METHOD OF THE PRODUCTION OF IMMUNOGLOBULIN HAVING HIGH CONTENT OF MONOMER

[75] Inventors: Tetsuro Sato, Kikuyo; Akinobu Funatsu; Komei Ohashi, both of Kumamoto; Shoji Ono, Kodaira; Tsunemasa Yoshida, Hachioji, all of Japan

[73] Assignee: Juridical Foundation The Chemo Sero-Therapeutic Research Institute, Osaka, Japan

[21] Appl. No.: 176,689

[22] Filed: Aug. 8, 1980

[30] Foreign Application Priority Data

Feb. 14, 1980 [JP] Japan .................................. 55-17370

[51] Int. Cl.$^3$ ................................................ C07G 7/00
[52] U.S. Cl. .................... 260/112 B; 424/85; 424/101
[58] Field of Search .................... 260/112 B; 424/101, 424/85

[56] References Cited

U.S. PATENT DOCUMENTS 4,059,571 11/1977 Tomibe et al. .................. 260/112 B
4,118,379 10/1978 Schmidtberger ............... 424/101 X

OTHER PUBLICATIONS

Acta Chemica Scandinavica, vol. 22, 1968, No. 2, 490-496, Hansson.

Primary Examiner—Howard E. Schain
Attorney, Agent, or Firm—Stevens, Davis, Miller & Mosher

[57] ABSTRACT

A method of the production of immunoglobulin having a high content of monomer from immunoglobulin-containing materials by a fractionation method, which comprises carrying out the fractionation in the presence of a water-soluble, basic nitrogen-containing organic compound having a dissociation constant (pKb) of 7 or less or an acid addition salt thereof, and thereby inhibiting by-production of undesirable aggregated molecules. The immunoglobulin has a high content of monomer and contains no or little aggregated molecules and hence can be used as a medicine in immune prophylaxis and immunotherapy without undesirable side effects and can be administered by intraveneous route, and further, is useful for the preparation of chemically treated immunoglobulin having a high content of monomer.

7 Claims, 2 Drawing Figures

METHOD OF THE PRODUCTION OF IMMUNOGLOBULIN HAVING HIGH CONTENT OF MONOMER

The present invention relates to a method of the production of immunoglobulin having a high content of monomer. More particularly, it relates to a method of the production of immunoglobulin from immunoglobulin-containing materials such as blood serum, blood plasma of human or other animals by a fractionation method, which comprises subjecting the immunoglobulin-containing materials to the fractionation in the presence of a water-soluble, basic, nitrogen-containing organic compound or an acid addition salt thereof, and thereby inhibiting by-production of aggregated molecules to give immunoglobulin having a high content of monomer.

In the present specification, "immunoglobulin" means mainly IgG (immunoglobulin G), and "monomer" means mainly IgG monomer.

It is well known that immunoglobulin is useful in immune prophylaxis and immunotherapy revealing excellent effects in the prophylactic and therapeutic treatment of various viral infections and bacterial infections. The immunoglobulin is usually produced by collecting from blood serum, blood plasma and other body liquids of human and other animals by fractionation methods. For example, the known fractionation methods are fractionation with alcohols at a low temperature [cf. E. J. Cohn et al; J. Am. Chem. Soc., Vol. 68, pages 459-475 (1946), and P. Kistler and H. Nitschmann; Vox Sanguinis, Vol. 7, pages 414-424 (1962)]; fractionation with rivanol (a tradename of acrinol)—ammonium sulfate [cf. J. Horejisi and R. Smetana; Acta Medica Scandinavica, Vol. 155, pages 65-70 (1956)]; and an ion-exchange chromatography [cf. H. Hoppe et al; Munchen Medizinische Wochenschrift, Vol. 34, pages 1749-1752 (1967)].

According to the known fractionation methods, however, the produced immunoglobulin contains 5 to 10% by weight of polymers and 10 to 20% by weight of dimer and has merely a monomer content of 70 to 85% by weight. Such an immunoglobulin containing a large amount of aggregated molecules such as polymers and dimer has serious drawbacks as mentioned below and is not suitable as a medicine.

When an immunoglobulin containing a large amount of aggregated molecules is administered to human or other animal body, the aggregated molecules show anticomplementary activity, i.e. they react with and activate the factors of the complement system, and anaphylatoxins and others released from the activated complement factors and induce various side effects such as hypotention, raising of body temperature, disorders of circulation system or the like. Accordingly, the immunoglobulin containing aggregated molecules is restricted in its administration route, that is, it can not be administered in intravenous route and can only be administered intramuscularly and by the latter route the immunglobulin shows its effect retardedly and does not allow quantity administration. When the immunoglobulin is administered in intramuscular route, the diffusion of the given immunoglobulin into blood vessel are limited, and hence, it is not expected to increase rapidly the blood level of the antibody and further, it might be possible that the aggregated molecules shows altered antigenicity. Thus, the conventional immunoglobulin obtained by the conventional fractionation methods has still problem of side effect even by intramuscular administration.

The immunoglobulin containing aggregated molecules has also a drawback in the preparation of medicine, because it is not suitable for lyophilization. That is, when the immunoglobulin containing aggregated molecules is lyophilized (freeze-dried), the lyophilized product can hardly be dissolved in a solvent (e.g. distilled water for injection) when used (it takes not only a longer time for the dissolution, but also some undissolved substances remain). Accordingly, the conventional immunoglobulin containing aggregated molecules is usually used as a medicine as it is in the form of a liquid, and a mercuric antiseptic is unavoidably added thereto in order to stabilize the sterility. In case of some specific immunoglobulin preparations such as an antitetanus immunoglobulin or anti-D immunoglobulin, they are prepared in the form of a lyophilized product by specific procedure, because a liquid preparation has too short life for such purposes, but these lyophilized preparations prepared by specific procedure have still problem due to its solubility.

In order to eliminate these drawbacks of the conventional immunoglobulin, there have been proposed various methods for producing immunoglobulin containing no or little aggregated molecules, for instance, a method of decomposing the aggregated molecules by treating the immunoglobulin with an enzyme [cf. H. E. Schultze et al; Deutsche medizinische Wochenschrift, Vol. 87, pages 1643-1650 (1962), J. T. Sgouris; Vox Sanguinis, Vol. 13, pages 71-84 (1967)]; a method of dissociating the aggregated molecules by adding the immunoglobulin to an acidic aqueous solution (pH 4) and hydrolyzing the aggregated molecules [cf. H. Koblet et al; Vox Sanguinis, Vol. 13, pages 93-102 (1967)]; a method of removal of the aggregated molecules by treating the immunoglobulin with high molecular compounds such as polyethylene glycol, hydroxyethyl starch or the like [cf. A. Polson et al; Vox Sanguinis, Vol. 23, pages 107-118 (1972), W. Schneider et al; Vox Sanguinis, Vol. 31, pages 141-151 (1976)].

Among these known methods, however, according to the method of treatment with a protease such as pepsin or plasmin, the aggregated molecules can almost be decomposed, but the monomer is also decomposed and is cut into pieces of F(ab')$_2$, Fab and Fc fragments, by which the half life of the immunogloublin in blood becomes shorter and further the biological activity of Fc portion is decreased due to cutting off of the Fc fragment. Moreover, according to the method of treatment with plasmin, they say that the activity of antibody is also decreased. Besides, according to the method of treatment with an aqueous solution of pH 4, the dissociation of the aggregated molecules is not completed and further the content of aggregated molecules is increased during the storage of the immunoglobulin thus obtained and the Fc portion might be partially denatured to result in deactivation thereof. According to the method of the treatment with high molecular compounds, monomer is also removed as well as the aggregated molecules, which results in lowering of yield of monomer, and further, there is a possibility of remaining of the high molecular compounds in the resulting immunoglobulin which may show a bad effect when such preparation is used as a medicine.

The present inventors have intensively studied on an improved method for eliminating the drawbacks of the conventional immunoglobulin and obtaining an immunoglobulin containing no or very little aggregated molecules and having a high content of monomer. As a result, it has been found that the desired immunoglobulin can be obtained by carrying out the fractionation of the immunoglobulin-containing materials in the presence of a water-soluble, basic nitrogen-containing organic compound or an acid addition salt thereof and thereby inhibiting formation of aggregated molecules.

An object of the present invention is to provide an improved method of production of immunoglobulin containing no or little aggregated molecules. Another object of the invention is to provide an improved fractionation method of immunoglobulin-containing materials with inhibiting formation of undesirable aggregated molecules. A further object of the invention is to provide an immunoglobulin having a high content of monomer which can be used as a medicine and can be administered by intraveneous route without undesirable side effects. These and other objects and advantages of the present invention will be apparent to persons skilled in the art from the following description.

According to the present invention, the immunoglobulin having a high content of monomer can be produced by subjecting the immunoglobulin-containing materials to fractionation method such as an alcohol fractionation at a low temperature, rivanol-ammonium sulfate fractionation, or ion-exchange chromatography in the presence of a water-soluble, basic nitrogen-containing organic compound or an acid addition salt thereof.

The method of the present invention can be applied to all immunoglobulin-containing materials, such as blood serum, blood plasma and other body liquids of human and other animals, and also extracts of various organs of human and other animals. The conventional fractionation methods are applicable without changing substantially the conditions such as temperature, pH, concentration of the precipitating agents such as alcohol, rivanol and ammonium sulfate. Besides, the water-soluble, basic nitrogen-containing organic compounds or the acid addition salts thereof may be added to the fractionation system at any stage, i.e. at the first stage or at any step during the fractionation procedure. For instance, in case of fractionation of blood plasma by the alcohol fractionation method, which is usually carried out by firstly treating the blood plasma with 8% ethanol to fractionate into Precipitate I and Supernatant I, treating the resulting Supernatant I with 20% ethanol to fractionate into Precipitate II+III and Supernatant II+III, treating the Precipitate II+III with 20% ethanol to fractionate into Precipitate II+IIIw and Supernatant II+IIIw, treating the Precipitate II+IIIw with 17% ethanol to fractionate into Precipitate III and Supernantant III, treating the Supernatant III with 25% ethanol to give the immunoglobulin (Precipitate II), and finally removing ethanol by lyophilization or other method, the basic nitrogen-containing organic compound or the acid addition salt therof may be added to the starting blood plasma or may be added at subsequent stages such as steps of the treatment of Supernatant I, Precipitate II+III or later steps. The Precipitate II+III obtained by the above alcohol fractionation method may be adoptable as a starting material for the production of immunoglobulin, and hence, the method of the present invention can advantageously be applied to such adoptable Precipitate II+III in the presence of a basic nitrogen-containing organic compound or the acid addition salt thereof. In view of inhibition of forming aggregated molecules by the basic nitrogen-containing organic compound or the acid addition salt thereof, it is preferable to be present the basic nitrogen-containing organic compound or the acid addition salt thereof in all fractionation procedure, and hence, the basic nitrogen-containing compound or the acid addition salt thereof is preferably added to the starting material and to each subsequent fractionation system.

The water-soluble, basic nitrogen-containing organic compounds used in the present invention have a dissociation constant (pKb) of 7 or less and include basic amino acids, (e.g. arginine, lysine, ornithine, citrulline), amide derivatives of neutral amino acids (e.g. leucinamide, glycinamide, alaninamide) or lower alkyl esters thereof having 1 to 4 carbon atoms in the alkyl moiety, guanidine, guanidine derivatives (e.g. methylguanidine, benzamidine), imidazole, imidazole derivatives (e.g. 2-methylimidazole), amine derivatives of glucose (e.g. D-glucosamine), alkylamines having 1 to 4 carbon atoms (e.g. methylamine, ethylamine, propylamine, isopropylamine, butylamine, tert-butylamine), or the like. Among these compounds, arginine is the most preferable compound. These basic nitrogen-containing compounds may be used alone or in combination of two or more thereof during the fractionation procedure. Different compound or different combination of two or more compounds may be used in each step of the fractionation procedure. Besides, the basic nitrogen-containing compounds may be used in the form of a free base or preferably an acid addition salt thereof such as a salt of an inorganic acid (e.g. hydrochloric acid, hydrobromic acid, nitric acid, sulfuric acid, phosphoric acid), which may be used as they stand or in the form of an aqueous solution.

The basic nitrogen-containing compounds or the acid addition salt thereof may be used in an amount which can show the favorable effect for inhibiting the formation of aggregated molecules and usually in an amount of 0.5 to 600 w/w %, preferably 5 to 200 w/w %, more preferably 10 to 100 w/w %, based on the weight of the total proteins contained in the immunoglobulin-containing materials to be treated. When the compounds are used in an amount of less than 0.5 w/w %, they can not achieve the desired effect, and on the other hand, when the amount is over 600 w/w %, they give undesirable effect on the fractionation procedure and the desired fraction is hardly purified. Very large amount is undesirable from the economical viewpoint, too.

The method of the present invention can be carried out by using apparatuses which are used for the conventional fractionation methods without modification thereof.

The immunoglobulin obtained by the present invention has a high content of monomer and a low anticomplementary activity, and the lyophilized product thereof has a good solubility in a solvent. The immunoglobulin of the present invention may contain the basic nitrogen-containing organic compounds or the acid addition salts thereof which are used in the fractionation procedure. Preferably, the immunoglobulin contains the basic nitrogen-containing compounds or the acid addition salts thereof of 5 to 100 w/w % based on the weight of total proteins. The remained basic nitrogen-containing compound or the acid addition salt thereof may also be removed by subjecting the immunoglobulin to dialysis or other appropriate procedure.

The lyophilized products of Examples 1 and 6 as disclosed hereinafter and also a lyophilized product of immunoglobulin obtained in the same manner as in Example 1 except that no l-arginine hydrochloride was used (reference example) were tested on various properties thereof including solubility. The results are shown in Table 1.

In the test, the content of monomer was measured as mentioned below, and other properties were measured in accordance with the provision as disclosed in "Minimum Requirement of Biological Products" 1973 by Ministry of Health and Welfare, Japanese Government.

Measurement of monomer content:

A 5 w/w % aqueous solution of immunoglobulin was subjected to a gel filtration with Sephadex G-200 (made by Pharmacia), and the absorbance of the resulting filtrate was measured at a wavelength of 280 nm, by which the protein concentration was measured and then the monomer content was calculated.

TABLE 1

| | Example 1 | Example 6 | Reference example |
|---|---|---|---|
| Monomer content (%) | 98.6 | 94.3 | 78.9 |
| Anticomplementary activity* | 17 units | 20 units | More than 90 units |
| Dissolution time (minute) | 3 | 3 | More than 10 |
| Undissolved substance | None | None | Observed |
| Purity (%) | 99 | 99 | 99 |
| Mobility (cm$^2$/Volt. sec) | $-1.3 \times 10^{-5}$ | $-1.3 \times 10^{-5}$ | $-1.3 \times 10^{-5}$ |
| Heating at 50° C. for 4 hours | No gelation was observed | No gelation was observed | No gelation was observed |
| Diphtheria antitoxin activity | 3 I.U./50 mg | 3 I.U./50 mg | 3 I.U./50 mg |
| Measles antibody activity | 15 I.U./50 mg | 15 I.U./50 mg | 15 I.U./50 mg |

[Remark]:
*It was measured according to Kabat Mayer process [cf. Experimental Immunochemistry, page 225 (1961)].

As is clear from the above test results, the immunoglobulin obtained by the present invention has a far higher content of monomer and a lower anticomplementary activity in comparison with that of the reference example. Besides, the lyophilized product of the present invention has a good solubility, and hence, the product of the present invention is suitable for the preparation of a medicine in the lyophilized form. Moreover, the product of the present invention is the same as the conventional immunoglobulin (reference) in the purity by electrophoresis, mobility, heat stability and antibody activities.

The immunoglobulin obtained by the present invention can be administered by intraveneous injection and can also be used as a starting material for the preparation of chemically treated immunoglobulin, such as sulfonation, alkylation, acylation or treatment with β-propiolactone. Using this starting material, there can be obtained a chemically treated immunoglobulin having a high content of monomer.

The same products of Example 1 and reference example as used in the above test were sulfonated by a known process [cf. Masuho et al; Vox Sanguinis, Vol. 32, page 175 (1977)], and the monomer content and anticomplementary activity of the sulfonated immunoglobulins thus obtained were measured. The results are shown in Table 2.

TABLE 2

| | Example 1 | Reference example |
|---|---|---|
| Monomer content (%) | 96.8 | 74.2 |
| Anticomplementary activity* | 12 units | 25 units |

[Remark]:
*It was measured by Kabat Mayer process [cf. Experimental Immunochemistry, page 225 (1961)].

As is clear from the above results, the product of the present invention can give an excellent sulfonated immunoglobulin.

The present invention is illustrated by the following Examples, but is not limited thereto.

EXAMPLE 1

The following procedure was done in accordance with the method by Cohn et al [cf. J. Am. Chem. Soc., Vol. 68, pages 459-475 (1946)].

In a human blood plasma (100 liters) was dissolved l-arginine hydrochloride in an amount of 0.5 w/v % and thereto was added ethanol in a concentration of 8 v/v %. The mixture was treated under the conditions of pH 7.2 and a temperature of −3° C. to give Precipitate I (1 kg in wet state) and Supernatant I. To the Supernatant I thus obtained was added ethanol until the concentration became 20 v/v % and the mixture was treated under the condition of pH 6.8 (regulated with acetic acid) and a temperature of −5° C. to give Precipitate II+III (4.5 kg in wet state) wherein immunoglobulin was contained and Supernatant II+III wherein alubumin was mainly contained. The Precipitate II+III fractions were dissolved in an aqueous solution containing l-arginine hydrochloride of 10 w/w % based on the weight of the Precipitate II+III (about 450 g of l-arginine hydrochloride), and thereto was added ethanol in a concentration of 20 v/v % under the conditions of a temperature of −5° C. and pH 7.2 to give Precipitate II+IIIw (4 kg in wet state). The Precipitate II+IIIw fractions were dissolved in an aqueous solution containing l-arginine hydrochloride of 10 w/w % based on the weight of the Precipitate II+IIIw (about 400 g of l-arginine hydrochloride), and thereto was added ethanol in a concentration of 17 v/v % under the conditions of pH 5.2 (regulated with acetate buffer) and a temperature of −6° C. to give Supernatant III. The Supernatant III was filtered, and to the filtrate was added ethanol in a concentration of 25 v/v % under the conditions of pH 7.2 and a temperature of −5° C. to give Precipitate II (1.2 kg in wet state). The Precipitate II was dissolved in a 10 w/v % l-arginine hydrochloride aqueous solution (1.2 liter), and the mixture was lyophilized. The resulting powder was dissolved in purified water and thereto were added glycine and sodium chloride. The mixture was sterilized by filtration and divided into amall portions, followed by lyophilization. The lyophilized product thus obtained contained l-arginine hydrochloride of about 40 w/w % based on the weight of total proteins.

The immunoglobulin obtained above was analyzed by means of a gel filtration analysis. The result is shown in the accompanying FIG. 1. The immunoglobulin had a polymer content of 0%, a dimer content of 1.4% and a monomer content of 98.6%.

Figure 2:
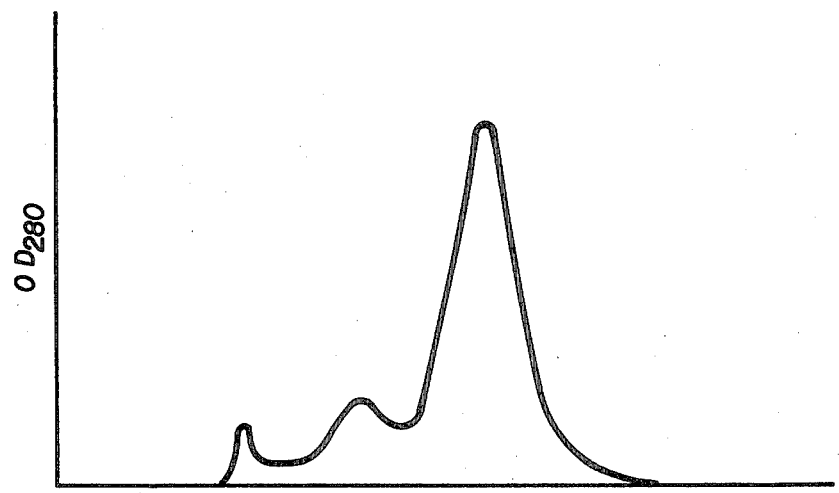

For comparison, the same fractionation procedure as above was carried out except that no l-arginine hydrochloride was used. The resulting immunoglobulin was analyzed by a gel filtration, likewise. The result is shown in the accompanying FIG. 2. The immunoglobulin of this reference had a polymer content of 3.8%, a dimer content of 17.3% and a monomer content of 78.9%.

EXAMPLE 2

The dried powder obtained in Example 1 was dissolved in distilled water and the solution was dialyzed against a saline solution to remove l-arginine hydrochloride completely. To the solution were added glycine, and the mixture was sterilized by filtration and divided into small portions, followed by lyophilization. The immunoglobulin thus obtained had a polymer content of 0%, a dimer content of 4.7% and a monomer content of 95.3%.

EXAMPLE 3

Precipitate II+III fractions (20 kg in wet state) obtained by an alcohol fractionation method were dissolved in an aqueous solution containing l-arginine hydrochloride of 10 w/w % based on the weight of the Precipitate II+III, and the mixture was treated in the same manner as described in Example 1 to give immunoglobulin which had a monomer content of 98.2%.

EXAMPLE 4

In a human blood plasma (1 liter) was dissolved l-arginine hydrochloride in an amount of 0.5 w/v %, and the solution was subjected to an alcohol fractionation at a low temperature according to the method of Kistler and Nitschmann [cf. Vox Sanguinis, Vol. 7, pages 414–424 (1962)]. Each fractionation step and lyophilization was carried out in the presence of l-arginine hydrochloride. The immunoglobulin thus obtained had a monomer content of 98.8%.

EXAMPLE 5

In a human blood serum (1 liter) was dissolved l-arginine hydrochloride in an amount of 0.5 w/v %, and the solution was subjected to a rivanol-ammonium sulfate fractionation method. Each fractionation step was carried out in the presence of l-arginine hydrochloride. The obtained precipitate containing immunoglobulin was dissolved in a 5 w/v % l-arginine hydrochloride aqueous solution and the solution was dialyzed to remove ammonium sulfate. The resulting solution was treated in the same manner as described in Example 1 to give immunoglobulin which had a monomer content of 94.7%.

EXAMPLE 6

Example 1 was repeated except that l-lysine hydrochloride was used instead of l-arginine hydrochloride. As a result, there was obtained immunoglobulin which had a monomer content of 94.3%.

EXAMPLE 7

Example 1 was repeated except that leucinamide hydrochloride was used instead of l-arginine hydrochloride. As a result, there was obtained immunoglobulin which had a monomer content of 96.2%.

EXAMPLE 8

Example 1 was repeated except that guanidine hydrochloride was used instead of l-arginine hydrochloride. As a result, there was obtained immunoglobulin which had a monomer content of 96.7%.

EXAMPLE 9

In the same manner as described in Example 1, except that imidazole hydrochloride was used instead of l-arginine hydrochloride, there was produced Precipitate II. The Precipitate II was treated in the same manner as described in Example 1 by using l-arginine hydrochloride to give immunoglobulin which had a monomer content of 93.2%.

What is claimed is:

1. In the production of immunoglobulin by a process which comprises fractionating a material containing immunoglobulin, the improved method which produces immunoglobulin having an aggregated molecule content of less than the amount required to produce undesirable side effects when administered intravenously, said improved method comprising directly fractionating said material containing native immunoglobulin in physical admixture with a water soluble, nitrogen containing compound which has a disassociation constant of 7 or less, or an acid addition salt thereof in a liquid phase to inhibit formation of aggregated molecules, and separating the resulting product from the said basic organic compound admixed therewith.

2. The method of claim 1 wherein the fractionation of native immunoglobulin is an alcohol fractionation at a low temperature.

3. The method according to claim 1, wherein the basic nitrogen-containing organic compound is a member selected from the group consisting of a basic amino acid, an amide derivative of a neutral amino acid or a lower alkyl ester thereof having 1 to 4 carbon atoms in the alkyl moiety, guanidine or a derivative thereof, imidazole or a derivative thereof, an amine derivative of glucose, an alkylamine having 1 to 4 carbon atoms, and a mixture of two or more thereof.

4. The method according to claim 1, wherein the basic nitrogen-containing organic compound is arginine.

5. The method according to claim 1, wherein the basic nitrogen-containing organic compound or the acid addition salt thereof is used in an amount of 0.5 to 600% by weight based on the weight of total proteins contained in the immunoglobulin-containing materials.

6. The method according to claim 5, wherein the amount of the basic nitrogen-containing organic compound or the acid addition salt thereof is in the range of 5 to 200% by weight based on the weight of total proteins contained in the immunoglobulin-containing materials.

7. The method according to claim 1 comprising a lyophilization step wherein the basic nitrogen-containing organic compound or the acid addition salt thereof is added to the fractionation system in each step of the fractionation and lyophilization.

* * * * *

UNITED STATES PATENT AND TRADEMARK OFFICE
CERTIFICATE OF CORRECTION

PATENT NO. : 4,384,993
DATED : May 24, 1983
INVENTOR(S) : Tetsuro SATO, et al

It is certified that error appears in the above-identified patent and that said Letters Patent are hereby corrected as shown below:

On the title page:

Under [73] Assignee: Should read as follows:

-- Juridical Foundation The Chemo Sero-Therapeutic Research Institute, Kumamoto, Japan and Teijin Limited, Osaka, Japan --

Signed and Sealed this

Twentieth Day of September 1983

[SEAL]

Attest:

GERALD J. MOSSINGHOFF

Attesting Officer     Commissioner of Patents and Trademarks